United States Patent [19]

Asturias

[11] Patent Number: 4,560,659
[45] Date of Patent: Dec. 24, 1985

[54] ETHANOL PRODUCTION FROM FERMENTATION OF SUGAR CANE

[76] Inventor: Carlos E. R. Asturias, 23rd Avenida 4-67 Zone 15, Guatamala City, Guatemala

[21] Appl. No.: 528,563

[22] Filed: Sep. 1, 1983

Related U.S. Application Data

[63] Continuation of Ser. No. 277,732, Jun. 26, 1981, abandoned, which is a continuation of Ser. No. 21,244, Mar. 15, 1979, abandoned.

[51] Int. Cl.$^4$ .............................................. C12P 7/14
[52] U.S. Cl. .................................... 435/162; 435/161; 435/940; 435/942
[58] Field of Search ................................ 435/161–165, 435/940, 942; 426/11; 127/43, 44

[56] References Cited

U.S. PATENT DOCUMENTS 3,093,548  6/1963  Coates et al. ................... 435/162
4,009,075  2/1977  Hoge ................................ 435/162

FOREIGN PATENT DOCUMENTS 402847  5/1934  Canada .
348549  3/1935  Canada .
341720  2/1942  Canada .

Primary Examiner—R. B. Penland

[57] ABSTRACT

A process for fermentation of sucrose wherein sucrose is extracted from sugar cane, and subjected to stoichiometric conversion into ethanol by yeast.

12 Claims, No Drawings

ETHANOL PRODUCTION FROM FERMENTATION OF SUGAR CANE

This application is a continuation of application Ser. No. 277,732 filed June 26, 1981 (now abandoned), which is a continuation of application Ser. No. 21,244 filed Mar. 15, 1979 (now abandoned).

BACKGROUND OF THE INVENTION

1. Field of the Invention

This invention relates to ethanol production from the fermentation of sucrose as it is naturally found in sugar cane. The invention relates to methods of fermenting cane pieces or particles, separation of the alcoholic yeast suspension and using said suspension to ferment again new or fresh cane pieces. This novel process whereby sucrose is extracted from cane and converted in situ in stoichiometric proportions, into ethanol, is for convenience referred to herein as "Exferm" process.

2. Description of the Prior Art

Ethanol production by fermentation is one of the oldest processes known to humankind, and has been employed principally for the elaboration of alcoholic beverages. It is said that Assyrian kings in 3500 BC had vineyards and wineries, see Hoogerheide, J. C. *Chem. Tech.* 7 (2) 94 (1977). The fermented beverages secured from sugar cane are usually associated with rum. The raw materials normally employed for this purpose are final or blackstrap molasses, high test molasses, virgin syrups, sugar cane juice and "panela" or the resulting solid from boiling raw juice. Rum manufacture has probably been in existence for more than 300 years and the first rum factories or distilleries were probably erected in the middle of the seventeenth century in the Caribbean islands; see, for example, Olbrich, H. *Ann. Technol. Agric.* 24 (3) 411–420 (1975). The process used by modern rum distilleries has not been subjected to major technical innovation in decades. This process consists basically of the following operations: (a) molasses handling, dilution, clarification and heat treatment, (b) anaerobic fermentation by a selected yeast strain, previously grown under controlled conditions, (c) yeast separation from the broth, (d) alcohol separation by distillation and eventual storage. For detailed descriptions and technical details see for example: Harrison, J. S. and Graham, J. C. J. "Yeast in Distillery Practice" in A. H. Rose and J. S. Harrison (Eds.) *"The Yeasts"* 3 (6) 283–348 (1970), Academic Press; Kampen, W. H. *Sugar y Azucar* 70 (8) 36–39, 42–43 (1975); L'Anson, J. A. P. *Process Biochem.* 11 (7) 35–39 (1971). In none of these references or in the related and similar technical literature is there any description of rum production directly from the fermentation of sugar cane, as the whole stack, fragments, small pieces, or a highly pulverized product. Even in very small or primitive sugar cane processing operations, there has always been the tendency to extract the juice or syrup from the solid fiber matrix. A recent article, Lipinsky, E. S. *Science* 199: 644–651 (1978), suggests, in general terms only, fermenting the extracted pith from cane directly with molasses. Tentscher, W., Owsianowski, R. P., Rudolph, K., and Bruschke, H., at the *International Symposium on Alcohol Fuel Technology*, held in Wolfburg, BRD, Nov. 21–23, 1977 (Papers 5-4, 5-5) have also suggested a process that has as an alternative approach the fermentation of crushed cane. It is noted that this is only a one step fermentation, however, and does not involve stoichiometric conversion of sucrose to ethanol from cane.

In sum, then, none of the foregoing references, nor the commercial practices known heretofore, in which molasses provides the preferred substrate for fermentation, teach the essentially stoichiometric conversion of sucrose in whole cane into ethanol by the repeated action of yeast thereon.

Accordingly, if means were provided for producing stoichiometric quantities of ethanol by fermentation of sucrose in comminuted sugar cane, the procedure would constitute a significant advance in the state of the art. If this result could be secured in a manner such that the fermentation proceeds in substantially as efficient a manner as where fermentation is effected in homogeneous liquid substrates an additionally unexpected and material advance in the relevant art would result.

SUMMARY OF THE INVENTION

Accordingly, an objective of this invention is to extract sucrose from cane and ferment it in situ to ethanol.

A further object of the invention is to provide ethanol in stoichiometric proportions from the sucrose extracted from sugar cane, in a single operation.

Other objects and advantages of the invention will become evident from the following description.

Accordingly, it has now been discovered, and this in a general manner constitutes the invention, that ethanol can be produced from sucrose as it is formed naturally in sugar cane by a process that involves reducing sugar cane to particulate form, introducing the resulting sugar cane particles into an aqueous medium to form a suspension therein; suspending a yeast strain therein to effect extraction of sucrose from said sugar cane and conversion by fermentation of said sucrose to ethanol in situ; recovering the resulting ethanol-yeast suspension and introducing further particulate sugar cane therein at a rate such that the conversion of the sucrose present in said suspension approaches and attains stoichiometric proportions.

DETAILED DESCRIPTION OF THE INVENTION

In sugar cane technology the recovery of sucrose from the cane plant requires the separation of juice from the fibrous material in the structure of the stalk. The tissue inside the rind of the stalk is a matrix of thin-walled parenchyma cells in which are imbedded the vascular bundles. This parenchymatous tissue is called the "pith". The rind and the vascular bundles are collectively referred to as the "fiber". Sucrose is present principally in the parenchyma storage cells. These cells are easily ruptured and the most commonly employed methods to extract the juice are by milling or crushing, hot water extraction or "diffusion", or a combination of both methods. In the diffusion method, cane is prepared by knife mills and roller crusher combinations.

The sugar cane for direct fermentation by yeast in accordance with the invention is conveniently prepared in any of the foregoing manners, provided however that the average particle size determined by standard procedures of sieve analysis of the comminuted cane is within the range of 0.25 centimeters (cms) to 4 cms., and preferably 0.25 cms. to 2.2 cms (3/16 to ⅞ inch) in diameter, or substantially so.

It has been discovered that a particle size within this range avoids an excessively slow rate of diffusion as would occur with larger particles while providing diffusion into the aqueous medium at a rate that is satisfactory to secure the objectives of the invention. Were the cells too small, on the other hand, even if difficulty in mass transfer were avoided, an excessively reduced apparent density would result necessitating an increase in the fermentor's volume such as to require ordinarily an uneconomic and inefficient operation thereof in context with the present invention.

The particular yeast inoculum employed in the practice of the present invention is not narrowly critical. Illustrative yeast strains useful and preferred in the practice of the invention are those maintained at the Central American Research Institute for Industry, Avenida La Reforma 4-47, Zone 10, Guatamala, C.A. (Instituto Centroamericano de Investigacion y Tecnologia Industrial, "ICAITI") as strains *Saccharomyces cerevisae* L-180; *Saccharomyces cerevisae* L-181; *Saccharomyces* L-200; *Saccharomyces* L-208, *Saccharomyces L-*140, and *Saccharomyces cerevisae* L-169 (hybrid 5-non-flocculant).

Particularly preferred are *Saccharomyces cerevisae* strains L-180 and L-181 which are also deposited at the Central Bureau Voor Schimmel Culture, Delft, Holland under the strain numbers CBS 2959 and CBS 1242, respectively.

During the initial fermentation step provided herein sucrose will first start to accumulate in the bulk of the solution as it migrates by diffusion from the parenchyma cells. Yeast will then start to utilize this sucrose as a source of carbon and energy and under anaerobic conditions will transform it stoichiometrically into ethanol and carbon dioxide. This sugar consumption will tend to decrease the bulk concentration of sucrose in solution, in the event its rate of consumption is faster than its rate of extraction. If this is the case, as the fermentation proceeds, sucrose extraction will proceed under the maximum concentration gradient existing at that time, because the sucrose concentration in solution in the suspension will be approaching zero. This fact will facilitate the extraction of the last amounts of sucrose in the cane. Also as fermentation proceeds, the ethanol bulk concentration in solution will increase. This alcoholic solution will start to leach out other cane non-sucrose components, helping in this way to disintegrate the solid-fiber matrix and enhancing, as a result, sucrose diffusion into the bulk of the solution.

After the cane has been prepared for fermentation, water must be added in the correct ratio in order to have a solid suspension in the fermentor. The cane:water ratio is critical to the process of the invention and may vary respectively within the range of 1:1.4 to 1:1.7. Too much water will dilute the final ethanol concentration, hence increasing the energy demand for purification and too little water will not produce an adequate cane suspension where yeast can function efficiently.

The temperature of the aqueous medium is elevated to one within the range of about 95° C. to 105° C., that is to boiling, for a period of from 5 to 10 minutes where, as is usually the case, it is desired to pasteurize the cane particles. The suspension is then cooled, to a temperature most desirably within the range of about 28° C. to about 35° C., at which temperature an inoculum of fermentation microorganism is introduced into the aqueous suspension.

The pH of the suspension is adjusted to within a range of about 4 to 7 employing, for example, hydrochloric acid or other standard reagent for this purpose, contemporaneously with addition of the yeast in order to provide optimum conditions for effective fermentation. In contrast to ethanol fermentation of molasses or cane juice or syrup where inorganic nitrogen must be added in order to secure adequate conversions to ethanol [see for example Bose, K. and Ghose, T. K. *Process Biochem.* 8 (2) 23 (1973)] the process of the present invention, wherein the yeast inoculum is added upon cooling to aqueous suspensions of particulate or comminuted cane obviates this need. While not intending to be limited to a particular theory of operation, it is believed that the yeast strains employed herein possess a proteolytic enzyme activity enabling them to utilize the organic nitrogen from the cane introduced into contact with the yeast in the practice of the invention.

Once the fermentation is complete and all the extractable sucrose has been, as a consequence, converted stoichiometrically to ethanol and carbon dioxide, the suspension can be separated easily on a sieve so that the solid cane particles will be retained and the yeast-ethanol suspension passed through. The entrapped liquid can be extracted substantially completely from the sucrose-stripped sugar cane pieces by applying a minimal pressure, illustratively from about 50 pounds per square inch (psig) to about 200 psig. Some yeast will still be held by adsorption and physical entrapment in the solid matrix. However this quantity is a minor fraction. The separation operation can be accomplished completely under aseptic conditions.

The yeast-ethanol suspension can be used again, in order to extract and ferment more sucrose present on a fresh batch of cane particles. In order to do so it is only necessary to charge both the newly comminuted cane particles and yeast-ethanol suspension to a fermentor. Sucrose will again be extracted and the higher ethanol concentration of the suspension will help in this process. The yeast will ferment stoichiometrically the sucrose into ethanol and carbon dioxide.

This sequence of events can be repeated as desired until the desired ethanol concentration is reached.

The ethanol is ultimately recovered from the ethanol-yeast suspension of the invention by standard filtration and distillation means well known to those skilled in the art to which this invention pertains. The ethanol so recovered is, of course, useful for many industrial purposes, in alcoholic beverages, and the like.

As sugar cane is only a 6 to 9 month crop in the tropics, the process can be utilized without modification to ferment sucrose present not only in fresh sugar cane but in previously dried and stored sugar cane, as well.

Having now generally described the invention, a further understanding can be obtained by reference to the following examples, which are presented for purposes of illustration and are not intended to be limiting.

EXAMPLE I

This example illustrates the initial extraction and fermentation step of the invention. Freshly cut cane stalks were broken by a pilot plant wood chipper. The cane chips were sifted and the particles having a size diameter of between 0.5 to 2.2 cm were separated and mixed again. This material represented around 90% by weight of the original cane. Approximately 150 g of this mixture of cane pieces or particles were placed in a 500 ml erlenmeyer flask together with 250 ml of tap water. The pH was adjusted to a value of 4.0–4.5 with HCl and the whole mixture or suspension heated until incipient boiling occurred. The suspension was cooled and inoculated with a 24 h old inoculum of a strain of *Saccharomy-* ces cerevisae (yeast) strain CBS 2959 (ICAITI L-180). The volume of inoculum was 40 ml, with 0.73 g/100 ml of total sugars, 2.89 g/100 ml of ethanol and 0.105 g (dry biomass)/10 ml. The erlenmeyer flask was incubated at 30° C. for 40 hours without agitation and after that time, the solid cane pieces were separated from the ethanolic-yeast suspension by a filter with a small cotton plug. The resulting liquid had an ethanol concentration of 3.05 g/100 ml; total sugars 0.03 g/100 ml and 0.052 g (dry biomass)/10 ml. From this data it was determined that the total ethanol produced was 12.29 g; the consumption of extractable sugars was 99.49%; the ethanol yield was 0.48 g. ethanol/g sucrose consumed; the total yeast biomass produced was 1.63 g and the yeast yield was 0.063 g (dry biomass)/g sucrose consumed.

EXAMPLE 2

This example illustrates the two step fermentation process of the invention. Freshly cut cane stalks were milled in a cane separator (pilot plant unit of the commercial machine from Lignex Products Group, Hawker Siddeley Canada Ltd.) and the "pith" was recovered, representing about 80% by weight of the fresh cane. Approximately 75 g of "pith" were placed in a 500 ml erlenmeyer flask together with 200 ml of tap water. The pH was adjusted to a value of 4.0–4.5 with HCl and the whole mixture was cooled and inoculated with a 24 h old inoculum of a strain of *Saccharomyces cerevisae* (yeast) strain CBS 2959. The volume of inoculum was 40 ml, with 1.45 g/100 ml of total sugars, 2.76 g/100 ml of ethanol and 0.085 g (dry biomass)/10 ml. The erlenmeyer flask was incubated at 30° C. for 40 hours without agitation and the solid cane pieces or particles were thereafter separated from the ethanolic-yeast suspension by a filter with a small cotton plug. The resulting liquid had an ethanol concentration of 2.67 g/100 ml; total sugars 0.02 g/100 ml and 0.029 g (dry biomass)/10 ml. From this data the total ethanol produced was determined to be 7.15 g; the consumption of extractable sugars was 99.51%; the ethanol yield was 0.59 g ethanol/g sucrose consumed; the total yeast biomass produced was 0.61 g. and the yeast yield was 0.049 g (dry biomass)/g sucrose consumed. One hundred and sixty nine (169) ml of this yeast-ethanolic suspension was then mixed with approximately 15 g of cane "pith" previously dried in a forced-air tray pilot plant dryer employing air at 60° C. to a final moisture of 2.00%. The flask was incubated at 30° C. for 24 hours. After that time the ethanol-yeast suspension was again separated by filtration through a cotton plug. The analysis of the liquid was 5.05 g/100 ml of ethanol; 0.06 g/100 ml of total sugars; and 0.059 g (dry biomass)/10 ml. The alcohol produced in this second fermentation was 4.68 g; 98.55% of the total extractable sugars were consumed; the yield was 0.63 g ethanol/g sucrose consumed; total biomass, 0.43 g and biomass yield 0.058 g (dry biomass)/g sucrose consumed.

Contrasting the teaching of the present invention with ethanol recovery from fermentation of sugar cane juice or molasses, it is noted that if complete or theoretical conversion of sucrose into alcohol is assumed and a content of sucrose in cane of 10% by weight of fresh cane is taken as an average and an equal amount of water weight is added to fresh cane the final content of ethanol in the solution after fermentation will be 2.65 g/100 ml. Sugar cane juice fermented according to conventional practices, and assuming a sucrose content of 10% by weight, will generate a final solution of 5.3 g/100 ml of ethanol. If any kind of molasses is diluted to 18% by weight of fermentable sugars, and fermentation proceeds according to the same known standard procedure the final ethanol concentration will be 9.54 g/100 ml. As ethanol has to be distilled off from the broths, a higher ethanol concentration in the feed of the tower will mean less energy to reach the same final ethanol concentration in the top effluent of the distillation equipment. It will be evident from the foregoing characterization why molasses has heretofore provided a preferred substrate to sugar cane juice or extract in ethanol recovery from sugar cane. It will also be evident from the foregoing discussion and examples that the present procedure, in which ethanol is removed directly from particulate or comminuted sugar cane is an aseptic extract-ferment procedure as efficient as where the fermentation is undertaken with a homogeneous substrate such as molasses, and represents a significant and unexpected improvement in the state of the art.

The terms and expressions employed herein are used as terms of description and not of limitation. There is no intention in the use of such terms and expressions of excluding equivalents of the features shown and described or portions thereof.

What is claimed is:

1. A process for the production of ethanol consisting of:
combining comminuted dried sugar cane stalks having an average particle size diameter of from about 0.25 centimeter, to about 4.0 centimeter, Saccharomyces yeast and water to form an aqueous suspension of said comminuted stalks, simultaneously extracting and fermenting sucrose from said comminuted stalks in situ to ethanol, separating said comminuted stalks from which sucrose has been extracted from said suspension and introducing additional dried sugar cane stalks from which sucrose is simultaneously extracted and fermented.

2. The process as claimed in claim 1 wherein said particles are present in said aqueous suspension in a ratio by weight of 1 part of sugar cane particles to from 1.4 to 1.7 parts of water.

3. A process as claimed in claim 1 wherein said comminuted sugar cane stalks are introduced initially into said aqueous medium in the absence of said microorganism and said aqueous medium is elevated to at least approximately 95° C. for a period of time sufficient to render said comminuted stalks aseptic; cooling said suspension and thereafter introducing said microorganism into said suspension.

4. A process as claimed in claim 1 wherein said particles have a diameter of from 0.5 cm. to 2.2 cm.

5. A process as claimed in claim 1 wherein at least two successive additions of dried comminuted sugar cane stalks are introduced into and removed from said suspension.

6. A process as claimed in claim 1 wherein said yeast strain is an inoculum of *Saccharomyces cerevisae*.

7. A process as claimed in claim 6 wherein said yeast strain is *Saccharomyces cerevisae* CBS 2959.

8. A process as claimed in claim 6 wherein said yeast strain is *Saccharomyces cerevisae* CBS 1242.

9. A process as claimed in claim 1 wherein said average particle size diameter is from 0.25 centimeters to 2.2 centimeters.

10. A process for the production of ethanol as claimed in claim 1 wherein said suspension is adjusted to a pH of about 4 to 7 upon addition of said yeast, said dried comminuted sugar cane stalk particles have an average particle size diameter of about 0.25 centimeters and are present in said suspension in a ratio by weight of 1 part to 1.4 to 1.7 parts of water and wherein entrapped liquid is recovered from said stalks upon separation thereof from said suspension by pressing said separated particles to a pressure of at least about 50 pounds per square inch.

11. A process as claimed in claim 10 wherein said pressure is within a range of 50 pounds per square inch to 200 pounds per square inch.

12. A process as claimed in claim 1 wherein extracting, fermenting and separating is repeated a plurality of times with new and additional amounts of dried comminuted sugar cane stalks.

* * * * *